(12) United States Patent
Hudson

(10) Patent No.: US 9,339,565 B2
(45) Date of Patent: May 17, 2016

(54) PROCESS FOR THE PREPARATION OF RADIOIODINATED 3-FLUOROPROPYL-NOR-β-CIT

(71) Applicant: MALLINCKRODT LLC, Hazelwood, MO (US)

(72) Inventor: Edmund C. Hudson, Clayton, MO (US)

(73) Assignee: MALLINCKRODT LLC, Hazelwood, MO (US)

( * ) Notice: Subject to any disclaimer, the term of this patent is extended or adjusted under 35 U.S.C. 154(b) by 0 days.

(21) Appl. No.: 14/496,376

(22) Filed: Sep. 25, 2014

(65) Prior Publication Data

US 2015/0087838 A1    Mar. 26, 2015

Related U.S. Application Data

(60) Provisional application No. 61/882,039, filed on Sep. 25, 2013.

(51) Int. Cl.
*A61K 51/00* (2006.01)
*A61K 51/04* (2006.01)

(52) U.S. Cl.
CPC ................... *A61K 51/0448* (2013.01)

(58) Field of Classification Search
CPC ................................ A61K 51/0448
See application file for complete search history.

(56) References Cited

U.S. PATENT DOCUMENTS

| | | | |
|---|---|---|---|
| 4,190,601 A | 2/1980 | Decker et al. | |
| 6,123,917 A | 9/2000 | Carroll | |
| 6,447,747 B1 | 9/2002 | Pirotte | |
| 6,548,041 B1 | 4/2003 | Meltzer et al. | |
| 2003/0109708 A1 | 6/2003 | Okano et al. | |
| 2010/0210843 A1 | 8/2010 | Hudson et al. | |

OTHER PUBLICATIONS

Neumeyer"[123I]-2B-Carbomethoxy-3B(4-iodophenyl)tropane: High-Affinity SPECT Radiotracer of Monoamine Reuptake Sites in Brain" Journal of Medicinal Chemistry. 1991, 34, 3144-3146.*
Neumeyer, John L. et al "N-B-Fluoroalkyl Analogs of (IR)-2B-Carbodethoxy-3B-(4-iodophenyl)-tropane (B-CIT): Radiotracers for Positron Emission Tomography and Single Photon Emission Computed Tomography Imaging of Dopamine Transporters" Journal of Medicinal Chemistry, 1994 , 37(11), 1558-61.*
Wilbur, J. Labelled Cpd. Radiopharm. 1982, 19(10), 1171.*
Chang, Louis W. "The neurotoxicology and pathology of organomercury, organolead and organotin." Journal of Toxicological Sciences, 1990 15 (Suppl. 4), 125-51.*
"A Guide to the Graphic Representation and Nomenclature of Chemical Formulae in the European Pharmacopoeia" European Pharmacopoeia 2011 2nd Edition.*
"How to name organic compounds using the IUPAC rules" Online "http://www.chem.uiuc.edu/GenChemReferences/nomenclature_rules.html" accessed Dec. 11, 2015.*
Swahn; Synthesis of unlabelled, 3H- and 125I-labelled β-CIT and its •-fluoroalkyl analogues β-CIT-FE and β-CIT-FP, including synthesis precursors; Journal of Labelled Compounds and Radiopharmaceuticals; 1996, pp. 675-685, vol. 38, No. 7.
Musachio; 3β-(p-Trimethylsilylphenyl)tropane-2βcarboxylic acid methyl ester: a new precursor for the preparation of [123I]RTI-55; Appl Radiat Isot; 1996; pp. 79-81, vol. 47, No. 1.
International Search Report and Written Opinion in Related PCT Application No. PCT/US14/57404 dated Dec. 11, 2014, 9 pages.
Bois et al., "Synthesis,radiolabeling, and baboon SPECT imaging 2beta-carbomethoxy-3beta-(3'[123I]iodophenyl) tropane([123]YP256) as a serotonin transporter radiotracer", Nucl. Med. Biol., 2008, pp. 53-59, vol. 35, No. 1.
Stehouwer et al., "Synthesis, Radiosynthesis, and Biological Evaluation of Fluorine-18 Labeled 2beta-Carbo (fluoroalkoxy)-3beta-(3'((Z)-2-haloethenyl)phenyl)nortropanes: Candidate Radioligands for in Vivo Imaging of Serotonin Transporter with Positron Emission Tomography", J. Med. Chem., 2008, pp. 7788-7799, vol. 51, No. 24.

* cited by examiner

*Primary Examiner* — David K. O'Dell

(57) ABSTRACT

The invention generally provides processes for the preparation of radioiodinated 3-fluoropropyl-nor-β-CIT. In particular, the process uses an arylsilane intermediate, thus avoiding the use of hexamethylditin, and reducing the number of steps previously required for the preparation of radioiodinated 3-fluoropropyl-nor-β-CIT from anhydroecgonine methyl ester. The invention also relates to the alkylation of a nortropane to the corresponding N-(3-fluoropropyl) analog using 3-fluoropropanal.

16 Claims, No Drawings

PROCESS FOR THE PREPARATION OF RADIOIODINATED 3-FLUOROPROPYL-NOR-β-CIT

CROSS REFERENCE TO RELATED APPLICATIONS

This application claims the priority of U.S. provisional application No. 61/882,039, filed Sep. 25, 2013, which is hereby incorporated by reference in its entirety.

FIELD OF THE INVENTION

The present invention relates to improved processes for the preparation of radioiodinated 3-fluoropropyl-nor-β-CIT.

BACKGROUND OF THE INVENTION

I-123 radioiodinated 3-fluoropropyl-nor-β-CIT (i.e., compound I) is a diagnostic agent useful for diagnosing and monitoring movement disorders and dementia, and has specific use in the diagnosis and monitoring of Parkinson's disease. I-123 radioiodinated 3-fluoropropyl-nor-β-CIT has the following structure:

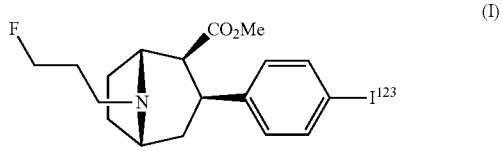

This compound can be prepared from anhydroecgonine methyl ester using a six step process, which relies on the conversion of an arylstannane precursor to the I-123 labeled compound. Such a process is generally disclosed in, for example, Swahn, et al., *Journal of Labelled Compounds and Radiopharmaceuticals*, 1996, Vol. XXXVIII, No. 7, p. 675-685. See also U.S. Pat. No. 6,447,747 (disclosing halogen-destannylation reactions). The reaction scheme commonly used to prepare I-123 radioiodinated 3-fluoropropyl-nor-β-CIT is set forth below:

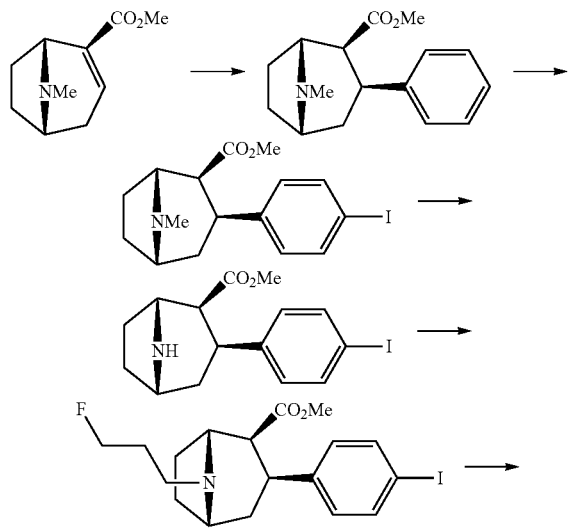

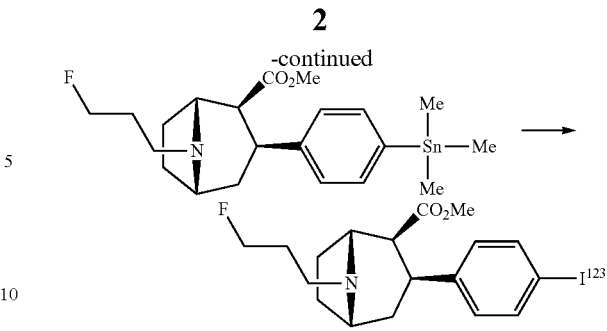

The preparation of the arylstannane precursor requires the use of the highly toxic tin reagent hexamethylditin. The safe use of hexamethylditin requires engineering controls and substantial personal protective equipment. There is thus a need for a process for the production of I-123 radioiodinated 3-fluoropropyl-nor-β-CIT that does not require the use of hexamethylditin.

Additionally, previously known methods for the conversion of a nortropane to the corresponding N-(3-fluoropropyl) analogue relied on alkylations using 3-fluoro-1-bromopropane. See, e.g., Swahn, et al., *Journal of Labelled Compounds and Radiopharmaceuticals*, 1996, Vol. XXXVIII, No. 7, p. 675-685. However, 3-fluoro-1-bromopropane is known to be an ozone depleting compound. There is thus a need for a process for the production of N-(3-fluoropropyl) analogs of nortropanes, and in particular I-123 radioiodinated 3-fluoropropyl-nor-β-CIT, that does not require the use of 3-fluoro-1-bromopropane.

SUMMARY OF THE INVENTION

In one aspect, the present invention is directed to a process for the preparation of compound (I) comprising the following reaction scheme:

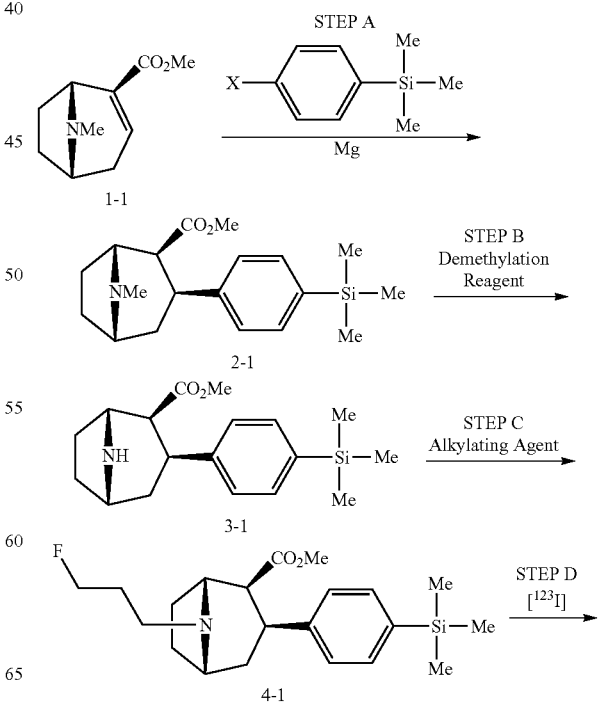

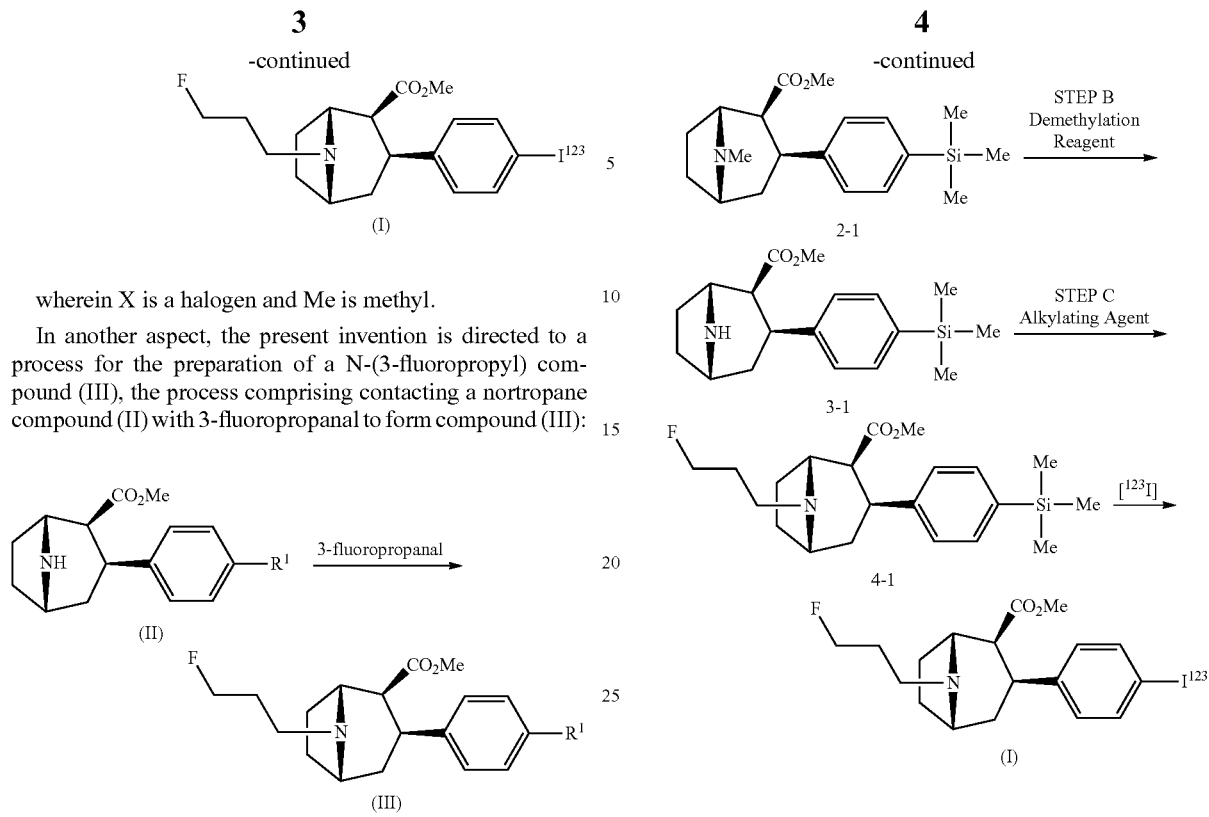

wherein X is a halogen and Me is methyl.

In another aspect, the present invention is directed to a process for the preparation of a N-(3-fluoropropyl) compound (III), the process comprising contacting a nortropane compound (II) with 3-fluoropropanal to form compound (III):

wherein $R^1$ is selected from the group consisting of halogen, {—}Si(CH$_3$)$_3$, and {—}Sn(CH$_3$)$_3$.

Other aspects and features of the invention are detailed below.

DETAILED DESCRIPTION OF THE INVENTION

The present invention relates to the preparation of I-123 radioiodinated 3-fluoropropyl-nor-β-CIT using an arylsilane intermediate. The process avoids the use of hexamethylditin, and has a reduced number of steps as compared to previously known processes for the preparation of radioiodinated 3-fluoropropyl-nor-β-CIT from anhydroecgonine methyl ester (compound 1-1). The present invention also relates to the alkylation of a nortropane to the corresponding N-(3-fluoropropyl) analogue using 3-fluoropropanal. The process avoids the use of the ozone depleting compound 3-fluoro-1-bromopropane.

Thus, in one aspect, the present invention provides a process for the preparation of compound (I) comprising the following reaction scheme:

Reaction Scheme 1:

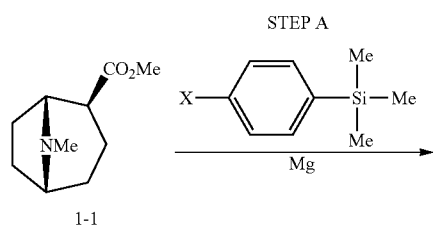

wherein X is a halogen, and Me is methyl.

In another aspect, the present invention is directed to a process for the preparation of a N-(3-fluoropropyl) compound (III), the process comprising contacting a nortropane compound (II) with 3-fluoropropanal to form compound (III):

wherein $R^1$ is selected from the group consisting of halogen, {—}Si(CH$_3$)$_3$, and {—}Sn(CH$_3$)$_3$.

Preparation of Compound (I)

In one aspect, the present invention relates to the preparation of I-123 radioiodinated 3-fluoropropyl-nor-β-CIT (compound I) using an arylsilane intermediate. Advantageously, the process avoids the use of hexamethylditin, and reduces the number of steps previously required for the preparation of radioiodinated 3-fluoropropyl-nor-β-CIT from anhydroecgonine methyl ester (compound 1-1).

Step A: Conversion of Compound 1-1 to Compound 2-1

Step A of the process involves or comprises the formation of an arylsilane precursor by reacting anhydroecgonine methyl ester (compound 1-1) with a halogen-substituted phenyltrimethylsilane in a Grignard addition reaction:

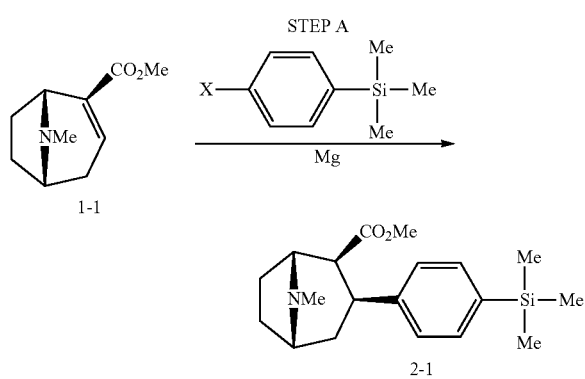

wherein X is a halogen, and preferably is I or Br.

(i) Formation of Grignard Reagent

A Grignard reagent may be prepared by contacting the halogen-substituted phenyltrimethylsilane with magnesium in the presence of a solvent. Suitable solvents for use in formation of the Grignard reagent include ethereal solvents, such as tetrahydrofuran, 2-methyltetrahydrofuran, tert-butyl methyl ether, diethyl ether, and the like. The halogen-substituted phenyltrimethylsilane is typically present in the solvent in at a molar concentration of from about 0.2 M to about 1.0 M.

The reaction mixture may optionally further include or comprise a compound for initiating formation of the Grignard reagent. Suitable compounds include an iodine crystal or ethylene dibromide. The compound is preferably included in the reaction mixture in an amount sufficient to catalyze formation of the Grignard reagent.

The reaction may be conducted at a variety of temperatures, for example, from about 30° C. to about 90° C., and preferably is conducted at reflux. The reaction is allowed to proceed until substantially complete, and typically for at least 30 minutes, and more typically from about 30 minutes to about 180 minutes, or from about 45 minutes to about 180 minutes. In some embodiments, the Grignard reagent forming reaction may be conducted under an inert atmosphere, such as argon or nitrogen.

(ii) Grignard Addition Reaction

The solution comprising the Grignard reagent is contacted with compound 1-1 to form an arylsilane precursor (compound 2-1). The Grignard reagent is preferably present in the reaction mixture in an amount of from about 2.2 to about 2.4 equivalents relative to compound 1-1 (e.g., about a 2.2:1 to about a 2.4:1 molar equivalent).

In some embodiments, an additional solvent may be added to the reaction mixture. Suitable solvents include methylene chloride, tetrahydrofuran, diethyl ether, 2-methyltrethydrofuran, tert-butyl methyl ether, and the like. In one embodiment, the solvent comprises methylene chloride and diethyl ether (e.g., diethyl ether added during preparation of the Grignard reagent) in a volume:volume ratio of about 1.2:1. Typically, compound 1-1 is present in the reaction mixture in a concentration of from about 0.1 M to about 0.3 M, and preferably is at a concentration of 0.17 M.

The reaction may be conducted at a variety of temperatures, for example, from about −40° C. to about −90° C., including from about −60° C. to about −85° C., and from about −75° C. to about −80° C. Preferably, the reaction is conducted at a temperature of −78° C. and allowed to warm to 0° C. The reaction is allowed to proceed until completed, typically for at least 20 minutes.

In some embodiments, the temperature of the reaction mixture may be further lowered following reaction, for example, to a temperature of from about −75° C. to about −80° C., and preferably to a temperature of −78° C. Following this second cooling, the reaction is quenched with an acid, such as trifluoroacetic acid.

In other embodiments, the reaction mixture is allowed to warm following addition of compound 1-1, for example, to from about 0° C. to about 22° C., and then cooled again to a temperature of from about −40° C. to about −90° C., and preferably to a temperature of −78° C. Following this second cooling, the reaction may be quenched with an acid, such as trifluoroacetic acid to obtain the arylsilane precursor (compound 2-1). Typically, the acid is added to the reaction mixture in a 1:1 molar ratio with the Grignard reagent.

Compound 2-1 may be isolated from the reaction mixture using any suitable technique known in the art, including, for example, filtration, ether extraction, rotary evaporation of solvent, chromatography, or combinations thereof.

Step B: Conversion of Compound 2-1 to Compound 3-1

Step B of the process involves or comprises demethylating the arylsilane precursor (compound 2-1) to form compound 3-1:

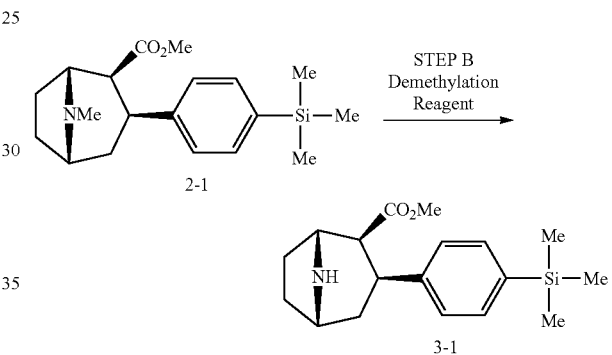

Suitable demethylation reagents include 1-chloroethylchloroformate, vinyl chloroformate, 2,2,2-trichloroethylchloroformate, and the like. The demethylation reagent is preferably present in the reaction mixture in an amount of from about 1 equivalent to about 10 equivalents, and more preferably in an amount of about 7 equivalents, relative to compound 2-1.

The reaction mixture may further include or comprise one or more aprotic solvent. Non-limiting examples of suitable aprotic solvents include 1,2-dichloroethane, ethyl acetate, toluene, chloroform, and combinations thereof. Preferably, the solvent is 1,2-dichloroethane or toluene. The solvent may be present in the reaction mixture in an amount of from about 1 mL to about 100 mL per gram of compound 2-1, and preferably in an amount of about 20 mL per gram of compound 2-1.

The reaction mixture may optionally further include or comprise an inorganic base. Non-limiting examples of suitable inorganic bases include sodium carbonate, potassium carbonate, sodium bicarbonate, potassium bicarbonate, and combinations thereof. The reaction mixture typically comprises the inorganic base in a molar ratio of compound 2-1 to inorganic base of from about 1:1 to about 1:6.

The demethylation reaction may result in formation of a carbamate intermediate compound. Thus, following the demethylation reaction, the mixture is typically concentrated and heated in methanol, to decompose the intermediate carbamate. In some embodiments, the reaction mixture may optionally further comprise one or more reagents to assist in the decomposition of the intermediate carbamate. Suitable reagents include combinations of zinc and acetic acid.

The reaction may be conducted at a variety of temperatures, for example, from about 60° C. to about 115° C., including from about 75° C. to about 115° C., and preferably is conducted at about 80° C. The reaction is allowed to proceed typically for at least about 1 hour, and preferably proceeds for about 3 hours.

In one embodiment, a base, such as N,N-diisopropylethylamine may be added to the reaction mixture after about 3 hours of reaction. The base is typically added in an amount of about 1 equivalent, relative to compound 2-1. The reaction mixture may then be reheated to a temperature of from about 60° C. to about 115° C., including from about 75° C. to about 115° C., and preferably about 80° C., and the reaction allowed to proceed for an additional 3 hours.

In one preferred embodiment, the demethylation reagent is 1-chloroethylchloroformate, and the reaction mixture contains about 7 equivalents of 1-chloroethylchloroformate relative to compound 2-1. Preferably, the reaction mixture is heated to 80° C. for 3 hours, followed by addition of N,N-diisopropylethylamine, and heating to 80° C. for an additional 3 hours.

Compound 3-1 may be isolated from the reaction mixture using any suitable technique known in the art, including, for example, filtration, chromatography, or combinations thereof.

Step C: Conversion of Compound 3-1 to Compound 4-1

Step C of the process involves or comprises the N-alkylation of compound 3-1 to form compound 4-1:

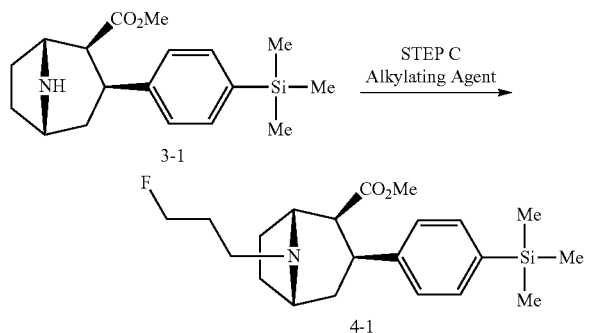

In this step, compound 3-1 is contacted with a suitable alkylating agent, such as 3-fluoro-1-bromopropane, 3-fluoro-1-iodopropane, or 3-fluoropropanal. In a preferred embodiment, the alkylating agent is 3-fluoropropanal. 3-fluoropropanal is commercially available, or may be prepared by oxidation of 3-fluoropan-1-ol using Dess-Martin periodinane or trichloroisocyanuric acid and TEMPO (i.e., 2,2,6,6-tetramethyl-1-piperidinyloxy). Typically, the reaction mixture will comprise from about 1 to about 3 equivalents of alkylating agent, relative to compound 3-1.

The reaction mixture may further comprise a solvent. Non-limiting examples of suitable solvents include ethyl acetate, 1,2-dichloroethane, acetonitrile, dichloromethane, chloroform, and combinations thereof.

When 3-fluoropropanal is the alkylating agent, the reaction mixture may include a reducing agent. Non-limiting examples of suitable reducing agents include sodium triacetoxyborohydride, sodium cyanoborohydride, and formic acid. Typically, the reducing agent is present in the reaction mixture in an amount of from about 2 equivalents to about 15 equivalents, relative to compound 3-1.

The reaction may be conducted at a variety of temperatures, for example, from about −20° C. to about 50° C., and typically is conducted at about 20° C. The reaction is allowed to proceed until substantially complete, and typically for from about 15 minutes to about 24 hours, and preferably for about 2 hours. Reaction completion may be determined using any suitable technique, such as HPLC.

Compound 4-1 may be isolated from the reaction mixture using any suitable technique known in the art, including, for example, solvent evaporation, filtration, chromatography, or combinations thereof.

Step D: Conversion of Compound 4-1 to Compound (I)

Step D of the process is a radioiododesilation reaction, in which the trimethylsilane moiety of compound 4-1 is replaced with I-123 to form compound (I):

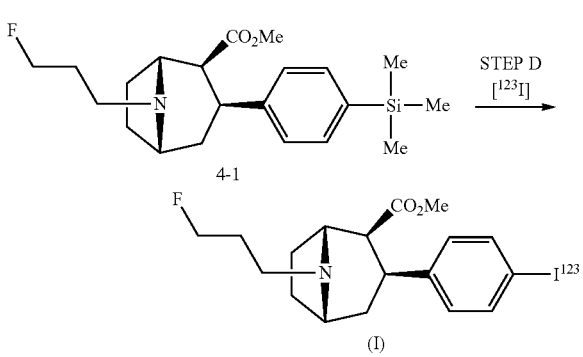

This reaction takes place by the addition of I-123, to a solution of compound 4-1 in a solvent optionally in the presence of an oxidizing agent. Optionally, the reaction mixture may further comprise a buffer, such as acetate.

Non-limiting examples of suitable solvents include methanol, acetic acid, trifluoroacetic acid, and acetic acid in ethanol.

Non-limiting examples of suitable sources of I-123 include sodium iodide (i.e., [$^{123}$I]NaI) and iodinemonochloride (i.e., [$^{123}$I]ICl).

Non-limiting examples of suitable oxidizing agents include Chloramine-T (i.e., (N-chloro-p-toluenesulfonamido)sodium), tert-butyl hypochlorite, peracetic acid, and combinations thereof.

In some embodiments, instead of an oxidizing agent, the reaction mixture may comprise a reagent, such as silver tetrafluoroborate, which increases the electrophilicity of the I-123 source.

Typically, the reaction mixture will comprise from about 0.6 to about 10 micrograms of compound 4-1 per mCi of I-123 from the I-123 source. In one particular embodiment, the reaction mixture may comprise, per mCi of I-123, from about 0.6 to about 10 micrograms of compound 4-1, about 3 microliters of trifluoroacetic acid, about 1.5 microliters of Chloramine-T, and about 0.25 microliters of methanol:acetic acid (99:1).

In one embodiment, the reaction mixture comprises [$^{123}$I]NaI, chloramine-T, and trifluoroacetic acid. In another embodiment, the reaction mixture comprises [$^{123}$I]ICl and silver tetrafluoroborate. In still another embodiment, the reaction mixture comprises [$^{123}$I]NaI and tert-butyl hypochlorite. In another embodiment, the reaction mixture comprises [$^{123}$I]NaI and peracetic acid in acetate buffer.

The reaction is typically conducted at a temperature of from about 21° C. to about 25° C., and allowed to proceed for at least about 15 minutes, and typically from about 15 minutes to about 2 hours.

The reaction may be quenched by addition of a base, such as NH₄OH, and compound (I) may be isolated using any suitable technique known in the art, such as solvent evaporation, chromatography, and combinations thereof. Suitable reaction conditions for Step D are described in, for example, Musachio, et al., *Appl. Radiat. Isol.*, 1996, Vol. 47, No. 1, p. 79-81.

Preparation of Compound (III)

In another aspect, the present invention relates to the alkylation of a nortropane to the corresponding N-(3-fluoropropyl) analogue using 3-fluoropropanal. The process advantageously avoids the use of the ozone depleting compound 3-fluoro-1-bromopropane.

Thus, in one embodiment, there is provided a process for the preparation of a N-(3-fluoropropyl) compound (III), the process comprising contacting a nortropane compound (II) with 3-fluoropropanal to form compound (III):

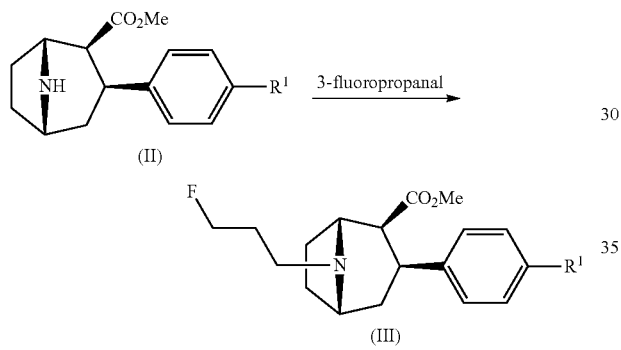

wherein $R^1$ is selected from the group consisting of halogen, {—}Si(CH₃)₃, and {—}Sn(CH₃)₃. Preferably, the halogen is I. In preferred embodiments, $R^1$ is I or {—}Si(CH₃)₃.

3-fluoropropanal is commercially available, or may be prepared by oxidation of 3-fluoropan-1-ol using Dess-Martin periodinane or trichloroisocyanuric acid and TEMPO (i.e., 2,2,6,6-tetramethyl-1-piperidinyloxy) according to the following reaction:

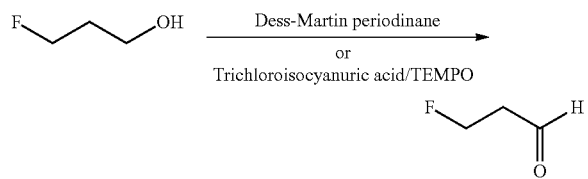

The reaction mixture may further comprise a solvent. Non-limiting examples of suitable solvents include ethyl acetate, 1,2-dichoroethane, acetonitrile, dichloromethane, chloroform, and combinations thereof.

The conversion of compound (II) to compound (III) may result in formation of an iminium intermediate (compound 1-2):

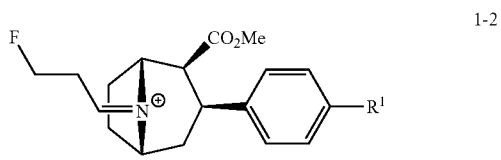

wherein $R^1$ is as defined above.

Thus, in some embodiments, it may be desirable to include a reducing agent in the reaction mixture to facilitate reduction of the iminium intermediate compound 1-2 to compound (III). Non-limiting examples of suitable reducing agents include sodium triacetoxyborohydride, sodium cyanoborohydride, and formic acid. Typically, the reducing agent is present in the reaction mixture in an amount of from about 2 equivalents to about 15 equivalents, relative to compound (II). The reducing agent may be added to the reaction mixture prior to or subsequent to reaction of compound (II) with the 3-fluoropropanal.

Suitable reaction conditions are described above for Step C of Reaction Scheme 1.

Compound (III) may be isolated from the reaction mixture using any suitable technique known in the art, including, for example, solvent evaporation, filtration, chromatography, or combinations thereof.

EXAMPLES

The following examples illustrate various iterations of the processes described herein.

Example 1

Production of Compound 2-1

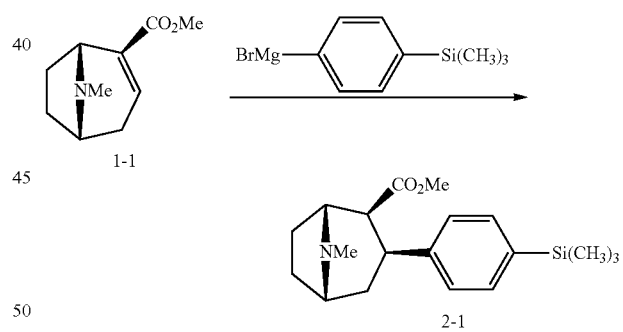

The Grignard reagent was prepared as follows: The reaction was initiated by adding about 0.6 mL (4 mmol) of (4-bromophenyl)trimethylsilane to a suspension of magnesium (0.286 g, 12 mmol) and an iodine crystal in 7 mL of ether and heating at reflux in an oil bath. After the reaction initiated, the mixture was diluted with 7 mL of ether and the remaining 1.7 mL (8 mmol) of (4-bromophenyl)trimethylsilane was added. The mixture was then heated at reflux for 1.5 hr.

After it had cooled to room temperature, the Grignard solution was added over 25 min to the solution of anhydroecgonine methyl ester (compound 1-1) (4.9 mmol) in dichloromethane (18 mL) cooled in a dry-ice/acetone bath (−78° C.). The mixture was stirred for an additional 25 min in the bath. The bath was then removed and the mixture was stirred for another 25 min.

The reaction was again cooled in the dry-acetone bath and 1.6 g (11 mmol) of trifluoroacetic acid in 4 mL of dichloromethane was added over 25 min. The mixture was allowed to warm to room temperature in the bath overnight.

The mixture was poured into a stirred mixture of a solution of 1:2 concentrated ammonium hydroxide:water (18 mL) and 18 mL of ethyl of ethyl acetate was added. An additional 4 mL of concentrated ammonium hydroxide was added to raise the pH to 10.0. The mixture was vacuum filtered through a 0.45 micron filter paper to remove a gel-like solid.

The layers were separated and the aqueous layer was extracted with two additional 18 mL portions of ethyl acetate. The combined ethyl acetate extracts were dried over sodium sulfate.

The solution was decanted from the ethyl acetate and concentrated on a rotovap. The residue was dissolved in EtOAc and filtered through a plug of silica 1.2 cm deep and about 2 cm in diameter. The plug was flushed with 100 mL of EtOAc. The filtrate was concentrated to a liquid, ~1.6 g.

The liquid residue was dissolved in about 4 mL of hexane and purified on a flash column of 25 g of silica packed in hexane. The column was eluted as follows:

150 mL of 1% of EtOAc and 0.5% TEA in hexane
150 mL of 2% of EtOAc and 1% TEA in hexane
400 mL of 3% of EtOAc and 1.5% TEA in hexane
150 mL of 4% of EtOAc and 2% TEA in hexane
100 mL of 5% of EtOAc and 2.5% TEA in hexane The column fractions of >98% purity were combined and concentrated give 0.38 g of compound 2-1.

Example 2

Demethylation of Compound 2-1

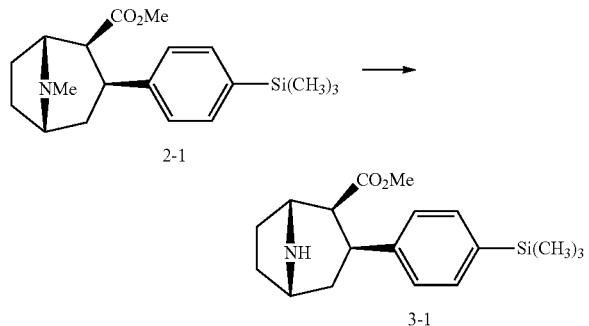

In a test tube, a 25 mg (0.065 mmol) portion of compound 2-1 was dissolved in toluene (0.5 ml). 1-chloroethyl chloroformate (50 microliters, 0.45 mmol) was added and the test tube was heated at 85° C. After 3 hrs N,N-diisopropyl-N-ethylamine (11 microliters, 0.065 mmol) was added to the test tube and the mixture was heated, with a timer set to turn off heating after 3 additional hours. The mixture was concentrated to a solid by rotovapping and the residue was dissolved in 0.6 mL of methanol. The solution was heated under reflux, heating block temperature 68° C., for 2 hours. The reaction was worked up by concentrating in vacuo, adding 2 mL of 1:1 water:concentrated ammonium hydroxide. The mixture was extracted with three 1 mL portions of dichloromethane. The combined organic layers of each extraction were dried over sodium sulfate. A sample of the organic extracts was analyzed by gas chromatography, which showed 80% compound 3-1.

Example 3

Preparation of N-(3-fluoropropyl) CIT

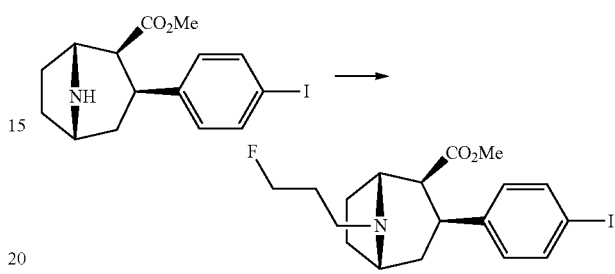

In a vial, 16 mg of 3-fluoropropanol was dissolved in 1.3 mL of dichloromethane. 1.3 mL of 0.3 M Dess-Martin periodane in dichloromethane was added. The mixture was stirred for 1 hr at room temperature. The mixture was diluted with 0.5 mL of EtOAc and filtered through a 0.45 micron syringe filter. The filtrate was chilled in a −30° C. bath and was added to a solution of 25 mg of nor-CIT containing 0.17 g of sodium triacetoxyborohydride and cooled in a −30° C. bath (the solution temperature was −21° C.). After 2 hrs, a sample of the reaction was worked up and analyzed by gas chromatography, which showed 75% N-(3-fluoropropyl) CIT.

When introducing elements of the present invention or the preferred embodiment(s) thereof, the articles "a", "an", "the", and "said" are intended to mean that there are one or more of the elements. The terms "comprising", "including", and "having" are intended to be inclusive and mean that there may be additional elements other than the listed elements.

As various changes could be made in the above compounds, products, and processes without departing from the scope of the invention, it is intended that all matter contained in the above-description shall be interpreted as illustrative and not in a limiting sense.

What is claimed is:

1. A process for the preparation of compound (I) comprising the following reaction scheme:

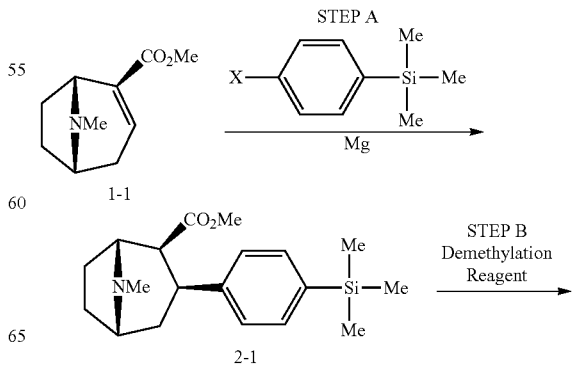

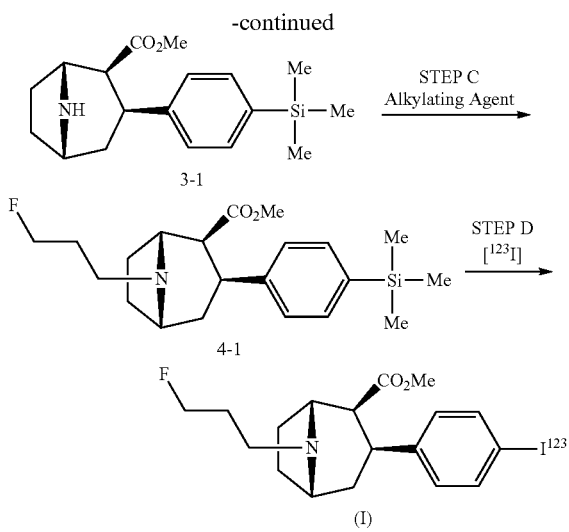

wherein:
X is a halogen, and
Me is methyl; and
wherein the alkylating agent is 3-fluoropropanol.

2. The process of claim 1, wherein X is Br or I.

3. The process of claim 1, wherein Step A comprises contacting a halogen-substituted phenyltrimethyl silane of formula:

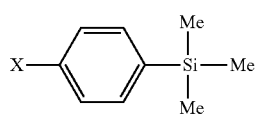

with magnesium to form a Grignard reagent.

4. The process of claim 3, further comprising contacting the Grignard reagent with compound 1-1 to form compound 2-1.

5. The process of claim 4, wherein the Grignard reagent is contacted with compound 1-1 at a temperature of from about −40° C. to about −90° C.

6. The process of claim 5, further comprising quenching the Step A reaction with trifluoroacetic acid.

7. The process of claim 1, wherein the demethylation reagent is selected from the group consisting of 1-chloroethylchloroformate, vinyl chloroformate, and 2,2,2-trichloroethylchloroformate.

8. The process of claim 1, wherein the reducing agent is selected from the group consisting of sodium triacetoxyborohydride, sodium cyanoborohydride, and formic acid.

9. The process of claim 8, wherein the reducing agent is present in the reaction mixture in an amount of from about 2 equivalents to about 15 equivalents, relative to compound 3-1.

10. The process of claim 1, wherein the reaction mixture of Step D comprises an oxidizing agent selected from the group consisting of Chloramine-T, tert-butyl hypochlorite, peracetic acid, and combinations thereof.

11. The process of claim 1, wherein the reaction mixture of Step D comprises iodinemonochloride and silver tetrafluoroborate.

12. A process for the preparation of a N-(3-fluoropropyl) compound (III), the process comprising contacting a nortropane compound (II) with 3-fluoropropanol in the presence of a reducing agent to form compound (III):

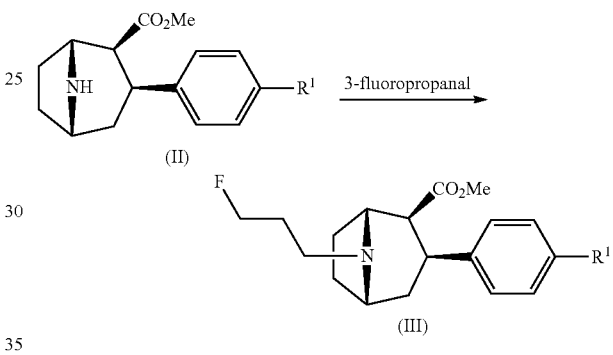

wherein $R^1$ is selected from the group consisting of halogen, $Si(CH_3)_3$, and $Sn(CH_3)_3$.

13. The process of claim 12, wherein the halogen is I.

14. The process of claim 12, wherein $R^1$ is $Si(CH_3)_3$.

15. The process of claim 12, wherein the reducing agent is selected from the group consisting of sodium triacetoxyborohydride, sodium cyanoborohydride, and formic acid.

16. The process of claim 12, wherein the reducing agent is present in the reaction mixture in an amount of from about 2 equivalents to about 15 equivalents, relative to compound (II).

* * * * *